United States Patent [19]

Dewey, Jr.

[11] 3,938,365

[45] Feb. 17, 1976

[54] DETECTING TRACE GASEOUS SPECIES ACOUSTICALLY IN RESPONSE TO RADIATION FROM AN INTENSE LIGHT SOURCE

[75] Inventor: C. Forbes Dewey, Jr., Belmont, Mass.

[73] Assignee: Massachusetts Institute of Technology, Cambridge, Mass.

[22] Filed: Nov. 29, 1973

[21] Appl. No.: 420,130

[52] U.S. Cl............ 73/24; 331/94.5 R; 331/DIG. 1
[51] Int. Cl.² ........................................ G01N 29/02
[58] Field of Search ........ 73/24; 250/343, 347, 345; 331/94.5, DIG. 1

[56] References Cited

UNITED STATES PATENTS

| 3,700,890 | 10/1972 | Kreuzer | 250/343 |
|---|---|---|---|
| 3,820,901 | 6/1974 | Kreuzer | 356/97 |

OTHER PUBLICATIONS

Kreuzer, Patell, Kenyon, *Science*, Vol. 177, pp. 347–349, July 28, 1972.
Kreuzer, Patell, Kenyon, *Science*, Vol. 173, pp. 45–47, July, 1971.
Kreuzer, *J. Appl. Phys.*, Vol. 42, pp. 2934–2943, June, 1971.

Primary Examiner—Herbert Goldstein
Assistant Examiner—Anthony V. Ciarlante
Attorney, Agent, or Firm—Arthur A. Smith, Jr.; Charles Hieken; Martin M. Santa

[57] ABSTRACT

An intense light source, preferably of high monochromaticity, having its beam modulated at a frequency corresponding to an acoustical resonant frequency of a sample chamber energizes the sample chamber along its axis. A photoelectric detector provides a signal related to this modulation for comparison with an acoustical signal provided by a microphone in the sample chamber. Means are provided for adjusting the modulation frequency so that it corresponds to the acoustical resonant frequency of the sample chamber as determined by a maximum in the amplitude of the amplified acoustical signal. An integrator may respond to the amplified acoustical signal to provide an indication of the energy absorbed by the medium in the sample chamber at the light wavelength and thereby the concentration of certain species in the sample chamber.

16 Claims, 5 Drawing Figures

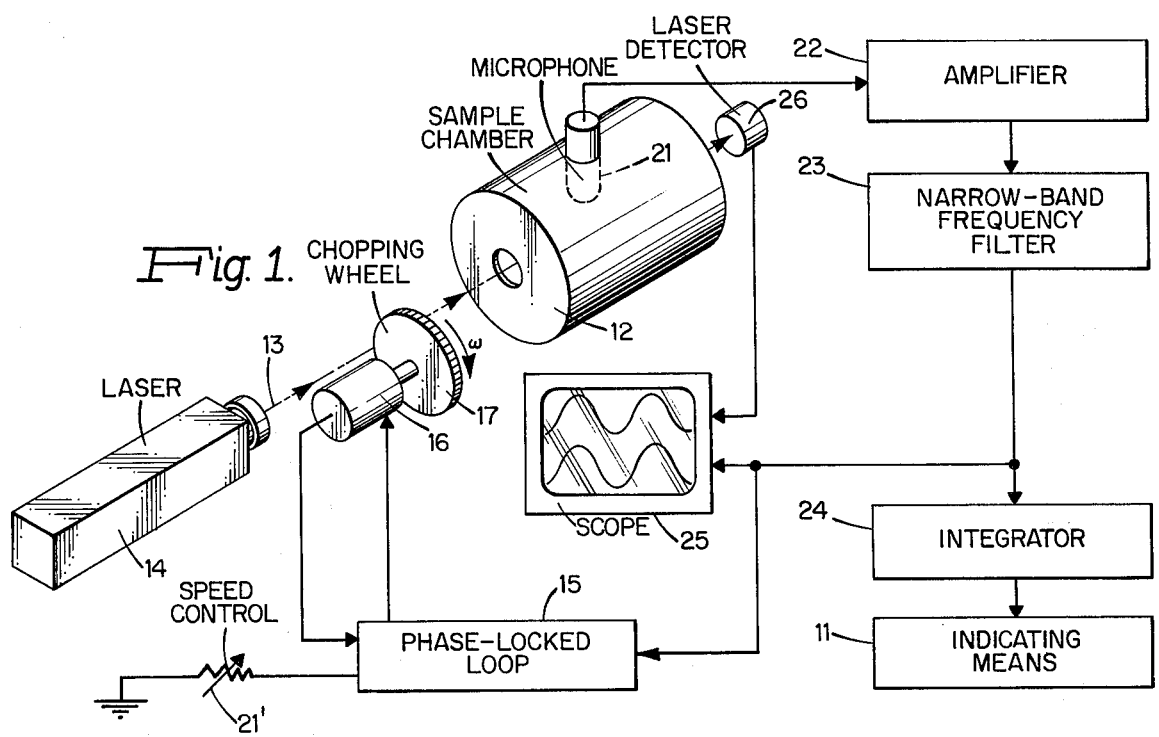
Fig. 1.
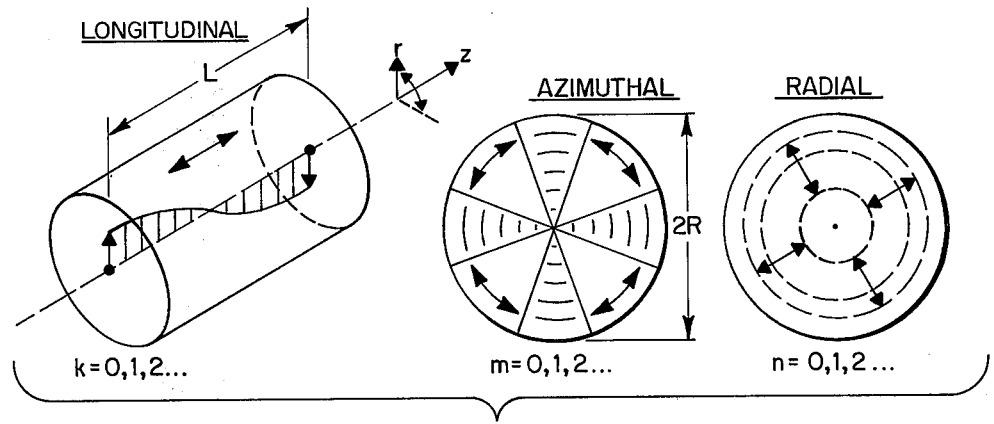
Fig. 2A.
| TYPYPICAL FREQUENCIES | | | | |
|---|---|---|---|---|
| | k | m | n | f (Hz) |
| FUNDAMENTAL FREQUENCIES | 1 | 0 | 0 | 1820 |
| | 0 | 1 | 0 | 1934 |
| | 0 | 0 | 1 | 4025 |
| HIGHER-ORDER MODES | 0 | 2 | 0 | 3208 |
| | 0 | 0 | 2 | 7380 |
| | 1 | 2 | 0 | 3808 |
Fig. 2B.

he present invention relates in general to detecting the character of a medium introduced in a sample chamber using acoustic signals produced by volumetric absorption of radiation and more particularly concerns novel apparatus and techniques for detecting atmospheric pollutants using acoustic signals produced by volumetric absorption of infrared radiation to achieve exceptionally high acoustic amplification and thereby facilitate detection.

DETECTING TRACE GASEOUS SPECIES ACOUSTICALLY IN RESPONSE TO RADIATION FROM AN INTENSE LIGHT SOURCE

This invention was made in the course of work performed under a contract with the Department of the Army.

BACKGROUND OF THE INVENTION

The present invention relates in general to detecting the character of a medium introduced in a sample chamber using acoustic signals produced by volumetric absorption of radiation and more particularly concerns novel apparatus and techniques for detecting atmospheric pollutants using acoustic signals produced by volumetric absorption of infrared radiation to achieve exceptionally high acoustic amplification and thereby facilitate detection.

It is known to measure trace gaseous constituents using acoustic signals produced by volumetric absorption of infrared radiation. Such a technique is described in an article by L. B. Kreuzer in *J. APPL. PHYS.*, 42, 2934 (1971). A laser or other source of radiant energy having a wavelength coincident with an absorption line of the species to be detected energizes a cell containing the sample mixture. The sample mixture absorbs radiation and converts it into thermal motion of the gas by intermolecular collisions. These collisions produce a pressure rise which may be detected by a sensitive microphone. The acoustic signal produced by the pressure rise is proportional to the concentration of the absorbing species. By modulating the beam of radiation at an audible rate, an easily detected periodic pressure signal is provided.

According to publications by Kreuzer, C.K.N. Patell and N.D. Kenyon in *SCIENCE*, 173, 45 (1971) and *SCIENCE*, 177, 347 (1972), this prior art approach yields detection sensitivities of a few parts per billion (ppb) for a number of important pollutants using selected gas laser wavelengths or a wavelength-tunable infrared spin-flip Raman laser as the excitation source. These publications reported encountering problems caused by background signal arising from spurious scattering and absorption by the optical windows and surfaces of the cell corresponding to a species concentration of 50–100 ppb, requiring a measurement accuracy of about 1% in the microphone signal amplitude to achieve the potential sensitivity of the apparatus.

A report dated Nov. 30, 1967 available from the Defense Documentation Center under AD 665674 at pages 32–44 suggests pulsing a laser beam along the axis of a cylindrical cavity at a rate corresponding to the cavity resonant frequency. The report does not tell how to do it in practice and states that success depends not only on the construction of a powerful laser with appropriate pulsing mechanism, but also on the construction of a highly sensitive acoustic detector coupled with the proper mode of many modes of oscillation of a cylinder.

Accordingly, it is an important object of this invention to provide improved methods and means for detecting the concentration of certain substances present in exceptionally small quantities in a medium being sampled.

It is another object of the invention to achieve the preceding object for detecting pollutants.

It is another object of the invention to achieve one or more of the preceding objects by exciting standing waves in an acoustic resonance chamber with essentially monochromatic energy modulated at a rate corresponding to the acoustic resonance of the chamber to provide high effective amplification facilitating the detection of substances in exceptionally small concentrations.

It is a further object of the invention to achieve one or more of the preceding objects with methods and means for maintaining the high gain despite changes in the resonant frequency of the acoustic chamber.

SUMMARY OF THE INVENTION

According to the invention, there is an acoustic resonance sample chamber means for receiving a medium having components to be detected. A source of substantially monochromatic radiant energy energizes the sample chamber means to cause pressure fluctuations contributing to standing acoustic waves within the chamber, the rate at which the radiant energy beam is modulated corresponding to one of the natural acoustic frequencies of the sample chamber. Means, such as comprising a microphone and signal amplifier, are provided for detecting the acoustic waves within the chamber and providing a corresponding amplified electrical signal. Means are provided for producing an output signal related to the amplitude of the electrical signal to provide an indication of the energy being absorbed in the sample chamber at the contemporary frequency of the incident radiant energy. Means are provided for adjusting the modulating rate to track a resonant frequency of the chamber. Means are also provided for measuring the attenuation of the incident radiant energy through the chamber.

Numerous other features, objects and advantages of the invention will become apparent from the following specification when read in connection with the accompanying drawing in which:

BRIEF DESCRIPTION OF THE DRAWING

FIG. 1 is a combined block-pictorial diagram illustrating the logical arrangement of a system according to the invention;

FIG. 2A illustrates longitudinal, azimuthal and radial modes in a cylinder;

FIG. 2B is a table relating typical frequencies and modal structures;

DETAILED DESCRIPTION OF PREFERRED EMBODIMENTS

Figure 3:
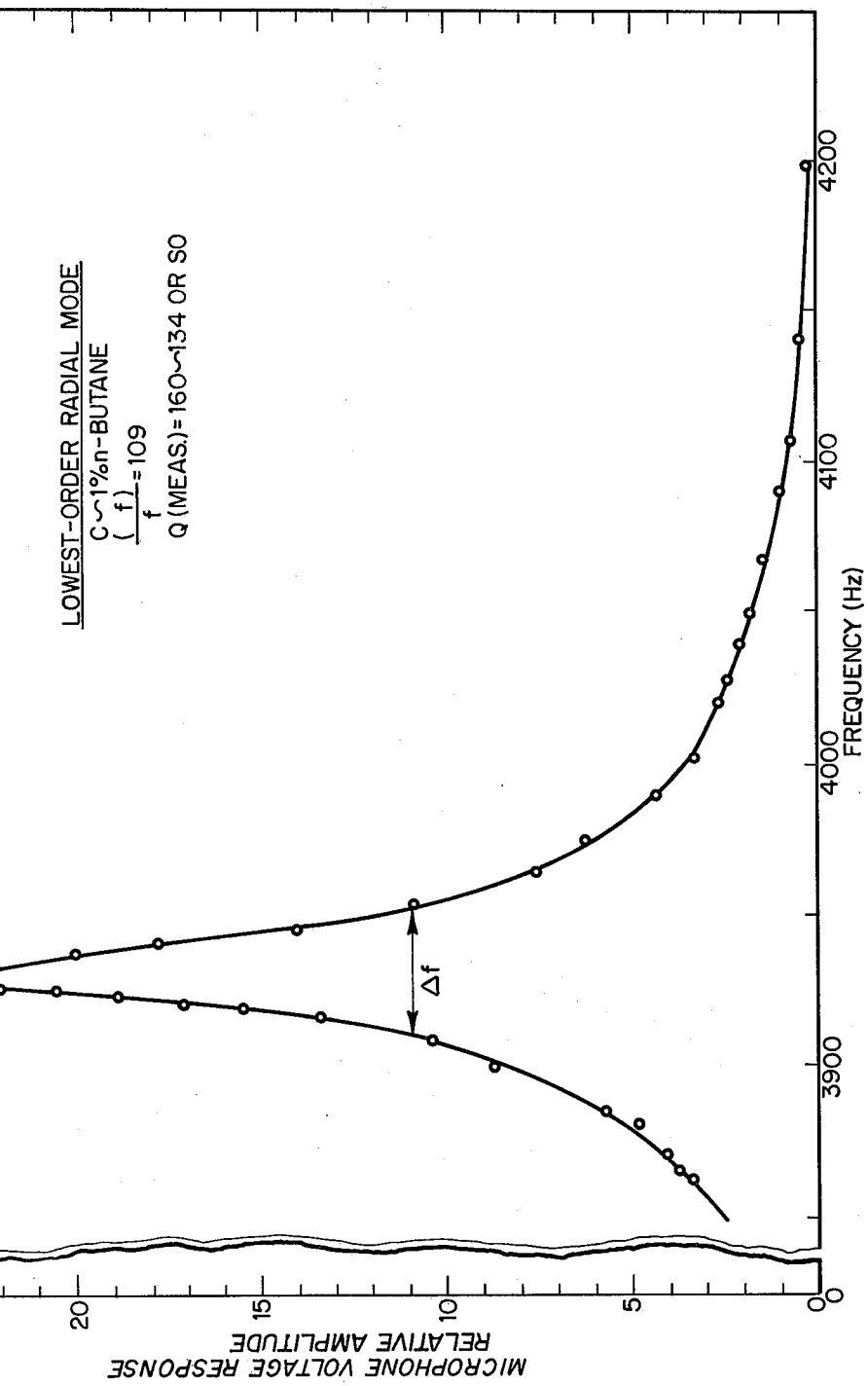
FIG. 3 shows signal output amplitude as a function of modulating frequency for a sample of 1% n-Butane.

Referring to FIG. 1, there is shown a combined block-pictorial diagram illustrating the logical arrangement of a system according to the invention. Indicating means 11 provides an indication of the degree of absorption of the medium then in sample chamber 12 for the wavelength or frequency of the monochromatic laser beam 13 provided by laser beam source 14.

A phase-locked loop 15 controls a brushless d-c motor 16 driving a fine-pitch gear 17 for chopping or modulating laser beam 13 at a rate corresponding to a resonant frequency of sample chamber 12. A resistor 21, typically in combination with a capacitor forming an RC network, coacts with phase-locked loop 15 to control the frequency of motor 16 at the desired rate.

A microphone 21 inside sample chamber 12, typically an electret microphone encapsulated with an impedance-matching FET, detects the acoustic signals produced in sample chamber 12 as laser beam 13 excites the resonant mode to produce an electrical signal from the microphone, typically in the audio frequency range, that is amplified by amplifier 22 and selectively transmitted by narrow band frequency filter 23 having its pass band centered about the selected resonant frequency of sample chamber 12. The output of narrow band frequency filter 23 is applied to an integrator 24 and to one input of a dual trance oscilliscope 25. The output of narrow-band frequency filter 23 may also be coupled to phase-locked loop 15 to control the chopping frequency to track the resonant frequency of the medium in the sample chamber by controlling the chopping wheel frequency to provide a maximum output from narrow-band frequency filter 23 in accordance with well-known techniques. The other input of oscilloscope 25 is connected to the output of photoelectric detector 26 that is energized by laser beam 13 after passing through sample chamber 12 to provide an output signal representative of the modulation introduced by chopping wheel 17 of amplitude corresponding to the beam attenuation after passing through the chamber. This signal is useful for detecting any changes in the amplitude of the signal incident to the sample chamber so that the output signal provided by indicating means 11 accurately reflects only the absorption in the sample chamber 12.

Speed control 21' is adjusted so that the output of filter 23 indicated on oscilloscope 25 is a maximum to insure that the chopping rate corresponds to the desired resonant frequency. The resonant frequency of sample chamber 12 depends upon the velocity of sound in the chamber which in turn is related to the medium, pressure and temperature. The temperature of the medium may change when heated by the incident radiant energy, the degree of heating being related to the degree of absorption. Adjusting speed control 21 so that the output from filter 23 is maximized as observed on oscilloscope 25 insures maximum system amplification. It is within the principles of the invention to adjust the speed of motor 16 automatically so as to maximize the output amplitude from microphone 21. It is also within the principles of the invention to control the incident radiation intensity provided by source 14 so that the output of detector 26 remains substantially constant. It is also within the principles of the invention to use electrical or optical means within the laser source itself to modulate the beam directly.

In a specific embodiment of the invention using a 3.39 $\mu$m He-Ne laser, the average laser power entering sample chamber 12 was about 0.6 mW. For convenience beam 13 made a single pass through the sample gas introduced into sample chamber 12. Sample chamber 12 was made of plexiglas with quartz exit and entrance windows and had a radius of 51 mm, length of 92 mm with the diameter of laser beam 13 equal to 2 mm. Microphone 21 had a diameter of 5 mm with an overall response of 1 mV/$\mu$bar and a broadband RMS noise level of about 5 $\mu$volts with a frequency response substantially flat between 100 Hz and 5 kHz. Microphone 21 was inserted into the chamber radially on the end of a 10 mm diameter rod, and the insertion distance adjusted for maximum microphone signal as indicated on oscilloscope 25. N-Butane was the trace absorbing species, exhibiting a substantial absorption cross section of about $4.8 \times 10^{19}$ cm$^2$ per molecule at atmospheric pressure at the unshifted 3.39 $\mu$m He-Ne laser line.

An advantage of exciting the fundamental radial mode is that the acoustical signal is nearly independent of axial or azimuth position. The radial position of the microphone may be readily adjusted for maximum signal. The axial location is preferably midway between the ends of the cylinder to minimize end effects.

An advantage of choosing the chamber to be cylindrical is that the radial resonances are nonharmonically related to each other and the other resonances. Although the larger maximum for the fundamental radial mode occurs on the axis, it has been found to be disadvantageous to locate the microphone on axis because the microphone produces an undesired assymetrical disturbance. It is preferred that the microphone be nearer the circumferential wall than the cylinder axis, and preferably at the wall where the smaller maximum occurs.

The natural acoustic resonances of the sample chamber may be determined by solving the wave equation in cylindrical coordinates. Using the boundary conditions of fully reflecting walls and bounded pressures along the cylinder axis at $r=0$, the normalized pressure distribution, P, within the cylindrical sample chamber 12 is given by:

$$P(r,\phi,z,t) = \cos(m\phi) \cos\left(\frac{k\pi z}{L}\right) J_m\left(\frac{\alpha_{m,n} \pi r}{R}\right) e^{-i\omega t}$$

$$\omega = \pi C_0 \left[\left(\frac{k}{L}\right)^2 + \left(\frac{\alpha_{m,n}}{R}\right)^2\right]^{1/2}$$

where the eigenvalues $k$, $m$ and $n$ define the logitudinal, azimuthal, and radial modes of the system as depicted in FIG. 2. $\alpha_{m,n}$ is the $n^{th}$ solution of the equation ($d J_m/dr$) = 0 at $r$ = R.

Referring to FIG. 2A there is shown pictorial representations of longitudinal, azimuthal and radial resonant standing wave patterns. FIG. 2B is a table relating typical frequencies in ambient air for designated fundamental and higher order modes of each standing wave pattern. As indicated above the speed of sound, $C_0$, changes slightly with concentration and temperature, but the resulting variations in the resonant frequency may be readily tracked (especially in the case of strong acoustic signals) by causing the phase-locked loop to be adjusted until the microphone signal as indicated on oscilloscope 25 is a maximum.

Referring to FIG. 3 there is shown a graphical representation of normalized microphone voltage response output amplitude indicated by indicating means 11 as a function of modulating frequency for the lowest-order radial mode ($k=m=0$, $n=1$) in which the acoustic Q or ratio of the resonant frequency to the bandwidth between half-power points, is 6. The results illustrated are for a concentration of about 1% n-Butane and demonstrate enhancement of the acoustic signal at resonance. Considering the effects leading to dissipation and dispersion of the standing wave, such as viscosity and heat conduction at the walls, imperfect wave reflection dispersion caused by the microphone stem and other effects, it is expected that a Q of between 200 and 300 is realizable in practical systems. The lowest-order radial mode is a preferred operating condition.

Figure 4:
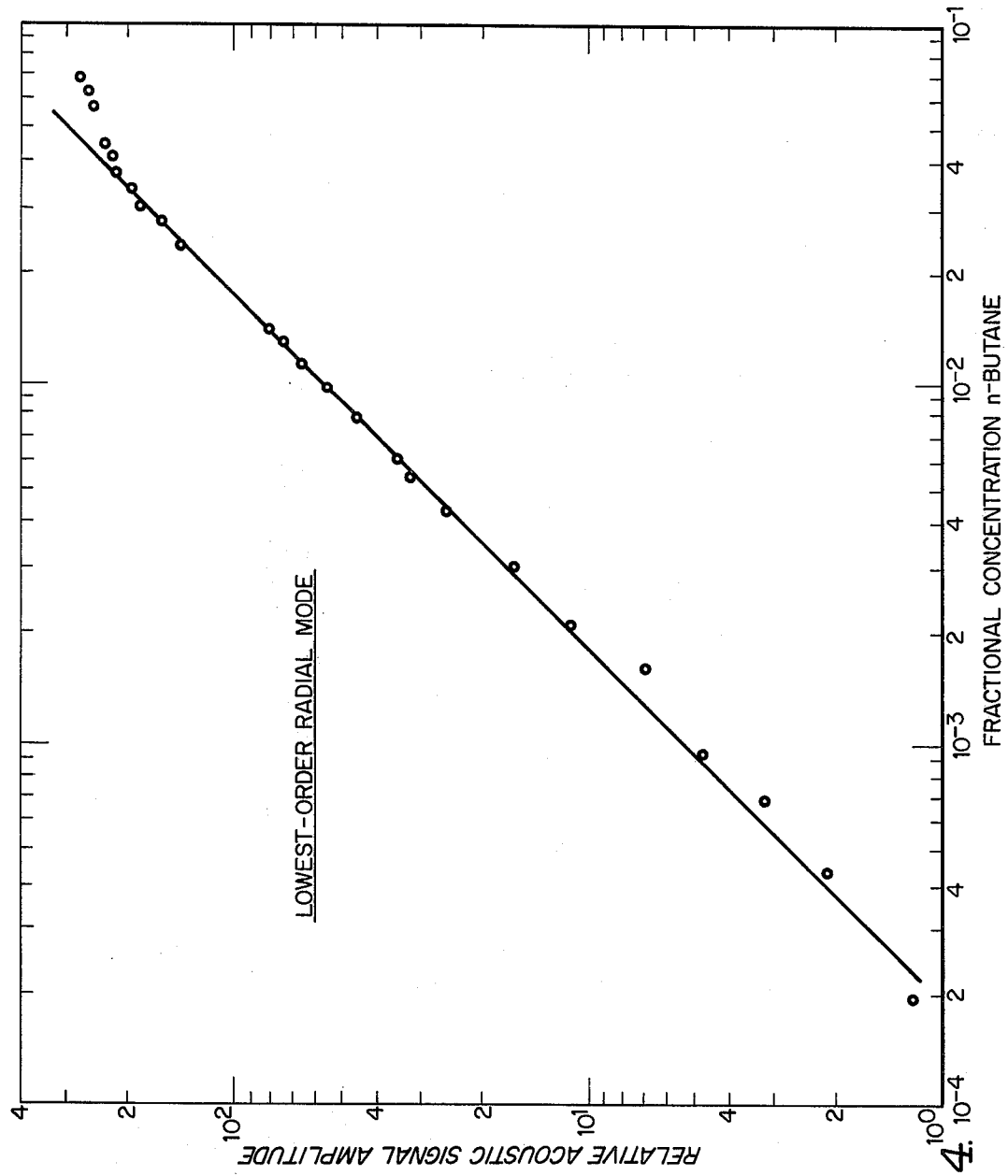
FIG. 4 shows output signal amplitude as a function of n-Butane concentration.

An important feature of the invention is that the microphone signal is a linear function of trace concentration. Referring to FIG. 4, there is shown experimental verification of this linear relationship where the trace component is n-Butane. The data of FIG. 4 were obtained by operating at the resonant frequency of the lowest-order radial mode. At resonance the signal is a linear function of the fractional concentration, C for $C < 2 \times 10^{-2}$. At higher concentrations significant absorption may occur near the beam entrance window leading to nonlinear absorption and excitation of longitudinal modes. The observed signal-to-noise ratio of microphone 21 was 10:1 at a fractional concentration, C, of $10^{-4}$ and an integration time of about 0.1 second for a lock-in amplifier used as the integrator 24.

Multiple passes of the laser beam may be used both to increase the fraction of incident radiation absorbed and a more favorable spatial coupling between the absorbed radiation and the desired standing wave. It is believed that a laser source of a milliwatt average power and a wavelength overlapping an absorption line of the measured species is capable of attaining sensitivities of a few parts per billion under practical conditions. This sensitivity enhances the utility of the invention in ambient pollution monitoring and industrial safety applications. The invention thus provides high sensitivity and relative simplicity for pollution monitoring. It may be advantageous to operate at sub-atmospheric pressure, down to approximately 20 Torr, to reduce pressure broadening from interfacing lines while modestly reducing absorption of a species to be measured.

A feature of the invention is that effects caused by absorption of the sample cell itself do not interfere with an accurate measurement because the signal detection circuit may be sharply tuned to the resonant frequency of the desired low-order radial acoustic mode. Absorption by the cell windows and by the walls of the chamber contribute primarily to waves whose spatial and temporal character are clearly distinct from the resonant wave and therefore do not contribute to the signal provided by indicating means 11.

While a laser modulated with a chopper is shown as the source of radiant energy in the exemplary embodiment illustrating the best mode now contemplated for practicing the invention, other sources of radiant energy and other modulation techniques may be used within the principles of the invention. For example, the source could be a broadband radiant energy source and could be internally modulated.

There has been described novel apparatus and techniques facilitating the detection of low concentrations of one or more species in a medium. It is evident that those skilled in the art may now make numerous other uses and modifications of and departures from the specific embodiments described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. Apparatus for detecting the presence of a species in a medium comprising,
   means defining a sample chamber for receiving said medium,
   a source of a beam of radiant energy incident upon said sample chamber for producing pressure waves therein of intensity related to the degree of absorption by said medium,
   means modulating said beam at a rate corresponding to a predetermined resonant frequency of said means defining a sample chamber,
   and acoustical detecting means for detecting the pressure wave signals produces in said sample chamber to provide an output signal representative of the degree of absorption of the medium in said sample chamber.

2. Apparatus for detecting the presence of species in a medium in accordance with claim 1 and further comprising,
   means for controlling said modulation rate to follow changes in the resonant frequency in said sample chamber.

3. Apparatus for detecting the presence of a species in a medium in accordance with claim 1 wherein said source provides a beam of substantially monochromatic radiant energy of cross sectional area less than that of said sample chamber.

4. Apparatus for detecting the presence of a species in a medium in accordance with claim 3 wherein said source comprises a laser.

5. Apparatus for detecting the presence of a species in a medium in accordance with claim 1 wherein said means for detecting comprises an electroacoustic transducer communicating with said chamber for providing an electrical signal in response to said pressure wave signals.

6. Apparatus for detecting the presence of a species in a medium in accordance with claim 1 wherein said sample chamber is cylindrical and said predetermined resonant frequency corresponds substantially to the fundamental radial mode of a pressure wave in said sample chamber.

7. Apparatus for detecting the presence of a species in a medium in accordance with claim 6 wherein said means for detecting comprises an electroacoustic transducer communicating with said chamber and closer to the circumferential wall of said chamber than the chamber axis.

8. Apparatus for detecting the presence of a species in a medium in accordance with claim 7 wherein the location of said transducer is substantially at said circumferential wall.

9. Apparatus for detecting the presence of a species in a medium in accordance with claim 1 wherein said means for modulating comprises a chopper wheel interposed between said source and said sample chamber.

10. Apparatus for detecting the presence of a species in a medium in accordance with claim 1 and further comprising means for causing said modulating rate to track said predetermined resonant frequency in the presence of variations of the latter.

11. Apparatus for detecting the presence of a species in a medium in accordance with claim 10 wherein said means for causing comprises a phase-locked loop.

12. Apparatus for detecting the presence of a species in a medium in accordance with claim 1 and further comprising,
    means for detecting the attenuation of said radiant energy in passing through said sample chamber.

13. Apparatus for detecting the presence of a species in a medium in accordance with claim 12 wherein said means for detecting the attenutation and said beam of radiant energy are aligned along the axis of said sample chamber.

14. Apparatus for detecting the presence of a medium in accordance with claim 13 wherein said source is a laser providing a beam of substantially monochromatic radiant energy of cross sectional area less than that of said sample chamber, said sample chamber is cylindrical and said predetermined resonant frequency corresponds substantially to the fundamental radial mode of a pressure wave in said sample chamber, said first-mentioned means for detecting comprises an electroacoustic transducer communicating with said chamber and closer to the circumferential wall of said chamber than to the chamber axis, and further comprising means for controlling said modulation rate to follow changes in said predetermined resonant frequency.

15. A method of using the apparatus of claim 1 which method includes the steps of introducing said medium into said sample chamber, exciting said medium with said beam of radiant energy modulated at said rate to produce said pressure waves therein, and detecting said pressure waves to provide said output signal.

16. A method in accordance with claim 15 and further including the step of controlling said modulating rate to follow changes in said predetermined resonant frequency.

* * * * *